United States Patent [19]

Staubli

[11] 4,253,834

[45] Mar. 3, 1981

[54] RIDER CLIP WITH OFFSET RETENTION FLAPS AND RETENTION BAR FOR DENTURE

[76] Inventor: Peter E. Staubli, Foster City, Calif.

[21] Appl. No.: 135,591

[22] Filed: Mar. 31, 1980

Related U.S. Application Data

[63] Continuation of Ser. No. 953,372, Oct. 23, 1978, Pat. No. 4,209,904.

[51] Int. Cl.³ .............................................. A61C 8/00
[52] U.S. Cl. ................................... 433/173; 433/177
[58] Field of Search .................... 433/177, 173, 172

[56] References Cited

U.S. PATENT DOCUMENTS

| 1,140,537 | 5/1915 | Skinner | 433/177 |
| 3,085,334 | 4/1963 | Bischof et al. | 433/180 |

*Primary Examiner*—Robert Peshock
*Attorney, Agent, or Firm*—Townsend & Townsend

[57] ABSTRACT

According to the invention, a device is provided for removably mounting dental bridge works and the like to an area to be bridged which comprises a retention bar having an arcuate transverse cross-section adapted to be secured to an abutment spanning an area to be bridged, and a clip adapted to be secured to a bridge piece and operative to resiliently couple onto the retention bar.

2 Claims, 4 Drawing Figures

RIDER CLIP WITH OFFSET RETENTION FLAPS AND RETENTION BAR FOR DENTURE

This is a Continuation of application Ser. No. 953,372, filed Oct. 23, 1978 now U.S. Pat. No. 4,209,904 issued July 1, 1980.

BACKGROUND OF THE INVENTION

1. Field of the Invention

This invention relates to a device for mounting a removable dental bridge or denture.

A removable dental bridge presents special problems in order to obtain sufficient cohesive force between the interengaged surfaces in the area to be bridged, high strength, long life, good hygiene, and to inhibit damage to living tissues and bone. In particular, it is difficult to obtain a balance of rigidity and flexibility insuring positive stabilization without damage to soft tissue and bone adjacent the area to be bridged. If the support is too rigid, the abutment, tissue and supporting bone structure can be damaged. If the support is too loose, then the denture may be inadvertently dislodged, causing inconvenience and embarrassment to the wearer.

It is not possible to increase size, strength and reliability of the mounting hardware substantially due to the space limitations. Moreover, bridge connectors are generally not easily adjusted to compensate for wear or minor changes in the features of the area to be bridged.

Therefore what is needed is a bridge connection structure which successfully overcomes the problems mentioned hereinabove, and particularly what is needed is an improved low cost system for mounting a removable dental bridge, denture or the like more acceptable to the intended application than devices heretofore known.

2. Description of the Prior Art

Dental clips are known for securing dentures and partial dentures to bars. One such system well-known in the art is the Dolder bar and clips. The Dolder bar comprises a rod having an egg-shaped transverse cross-section, and the clip comprises an open tubular segment having a horseshoe-shaped transverse cross-section.

The Dolder clip is subject to undersired loosening from the bridge piece into which it is embedded because the clip has no means for securing the clip to the material of the bridge piece other than the smooth outer surfaces of the clip walls. Moreover, the structure lacks provision respecting control of flexure of the side walls, which is potentially a problem should adjustment be required.

Another mounting system known to the art is the Ackermann bar and clip. The Ackermann bar may be either round or egg-shape in transverse cross-section. Of particular interest is the Ackermann clip. It comprises an open tubular segment having a horseshoe shape in cross-section, but it is characterized by a flare at the margins of the outer sides and by laterally disposed retention wings. The retention wings are tapered segments cut from the sides of the clip. The Ackermann clip and bar are intended to attach in a manner allowing a certain amount of play between parts of the prosthetic device.

The Ackermann clip is however subject to shortcomings. For example, the lateral retention wings, being tapered, do not always firmly seat in the acrylic material which is typically the compositon of the bridge piece. Furthermore, the wings, being formed by cut-outs from the sides of the clips, appear to weaken the clip sides somewhat. The cavities resulting from the cut-outs are also subject to accumulation of debris, which require special cleaning attention. A further significant limitation of the Ackermann clip is the difficulty of mounting the Ackermann clip in a relatively narrow prosthetic device. The wings have been found to interfere with normal investing (molding) processes. The wings must therefore be cut off or so severely bent as to be rendered ineffective to firm seating in the acrylic mold material.

A further example of a device for mounting a dental bridge is found in U.S. Pat. No. 3,429,043. Therein a bridge mounting device is described comprising a bar having a rectilinear transverse cross-section and a corrugated surface which is adapted to be mounted under tension between interfaces of a relatively rigid sleeve. Such a device does not provide for play or for adjustment, and therefore appears to be subject to the problems of loosening with age and wear and damage to tissue and the like, as hereinabove discussed.

SUMMARY OF THE INVENTION

According to the invention, a device is provided for removably mounting dental bridge works and the like to an area to be bridged which comprises a retention bar having an arcuate transverse cross-section adapted to be secured to an abutment spanning an area to be bridged, and a clip adapted to be secured to a bridge piece and operative to resiliently couple onto the retention bar.

The clip in its preferred embodiment is an open tubular segment of a longitudinal extent not substantially exceeding the breadth of a tooth and having a horseshoe-shaped transverse cross-section. Each clip includes two flaps protruding outwardly from opposing ends of the tubular segment on opposite sides of a dorsal plane substantially bisecting the segment. The outer portions of the side walls of the segment are provided with grooves parallel with the dorsal plane to concentrate lateral flexure along the grooves.

In particular embodiments of the invention, the longitudinal margin of each of the side walls is provided with a lap seam to protect tissue abutting on the clip against damage from rotational movement of the clip on the retention bar, limited rotational movement being a particular object of the invention. For this purposes, the preferred embodiment of the retention bar is a rod having a circular transverse cross-section.

The retention flaps are flared outwardly from the dorsal plane in order to present a larger area at the extreme ends of the flaps which more effectively seat in the material of the bridge. The flaps, however, do not impinge across the dorsal plane so that the flaps can overlap one another when the clips are abutted end to end.

Still further according to the invention is a method for mounting clips of the above type in a bridge piece during molding in a manner permitting subsequent adjustment and flexure of the side walls. The method comprises shrouding the side walls of the clip in a filler material of the type subsequently described to the level of the grooves, leaving only the flaps and adjacent portion of the clip exposed, covering the clips with wax material such that only the flaps and adjacent portions of the clips are embedded therein, packing plaster material about the wax material and the filler material, evacuating the wax material from the investment of plaster material (e.g., by melting it), and substituting denture material for the wax material in the investment. Thereafter the filler material is removed to expose the side walls up to the level of the grooves, the grooves serving as so-called "block-out lines" defining the border of the mold material.

One of the objects of the invention is to provide a rider clip in a denture or the like, such as a tissue filler or tooth, which can be securely embedded in the prosthetic material. For this purpose, flaps are provided which protrude from arcuate clips.

A further object of the invention is to provide compact seating of secured clips with flared flaps as above. This is achieved by providing the flaps at opposing ends of the retention clips such that they are offset on opposing sides of a dorsal plane permitting clips to be abutted end to end without interference between the retention flaps. The mounting of retention flaps at the end wals of the clips eliminates problems associated with lateral retention flaps.

One of the further objects of the invention is to provide a mounting system for use mainly with overdentures, partial dentures and tissue replacement where secure mounting of a prosthetic device in a relatively small space is a requisite. The bars for example may be contoured to the tissue and connect between abutments, root cap copings, or can be mounted to a single root cap coping in a small space.

A still further object of the invention is to provide a rider clip system with resilient, adjustable mounting. This is achieved by providing means for exposing a portion of the side walls of the clips and providing the side walls with means for constraining flexure to a longitudinal margin, particularly along a designated line.

A still further object of the invention is to provide a denture at substantially reduced cost as compared to systems known heretofore. This is accomplished by the use of relatively inexpensive materials made possible by an improved design. For example, the clips may be formed of corrosion-resistant, mechanically resilient material such as stainless steel, and the mold material may be an acrylic polymer material. The provision of retention flaps enhances the ability to use an acrylic polymer as the prosthetic material since the clips can be more securely seated in the acrylic material.

A still further object of the invention is to promote psychological security in the patient. This is accomplished by providing a prosthetic device which includes clips and retention bars capable of securing the prosthetic device within a flexibility-rididity range of comfort, the tension of the device being relatively easily adjusted. Still further, the security of the patient is enhanced by reduced wear and extended lifetime of a prosthetic device incorporating clips and bars according to the invention.

Other objects and advantages of the invention will be apparent upon reference to the following detailed description of the invention taken in conjunction with the accompanying drawings.

DETAILED DESCRIPTION OF PREFERRED EMBODIMENTS

Figure 1:
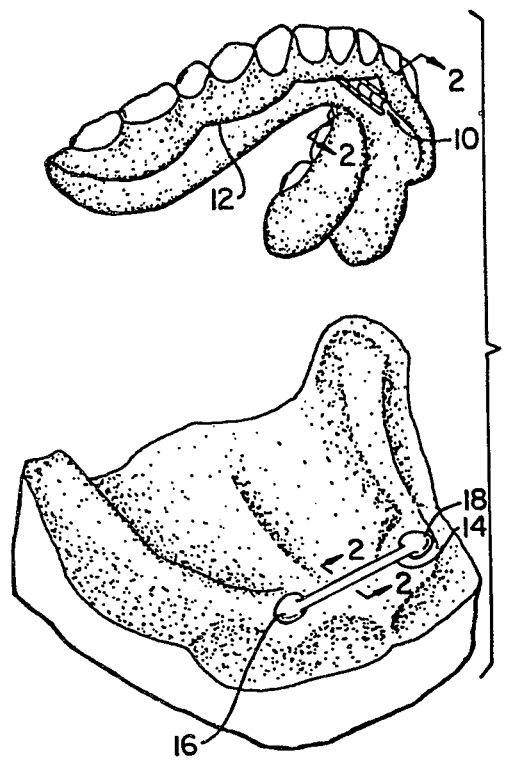
FIG. 1 is a perspective view of a denture and abutment arrangement according to the invention.

Referring to FIG. 1, the invention comprises a dental bridge coupling of at least one clip 10 embedded in a denture 12 and a retention bar 14 secured to one or more abutments 16, 18, such as a root cap coping. The invention may be used with full or partial dentures or with tissue replacement.

If the area to be bridged is greater than the breadth of a single tooth, the retention bar 14 may span between abutments 16, 18, as shown in FIG. 1. If the area to be bridged is however less than the breadth of a single tooth, the retention bar 14 may be mounted directly over an abutment (not shown).

Figures 2A, 2B:
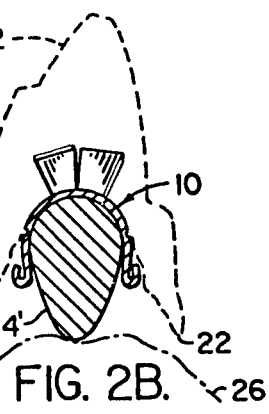
FIG. 2A, 2B and 2C illustrate first, second and third embodiments of the invention in transverse cross-section along section lines 2—2 of FIG. 1.
Figure 2C:
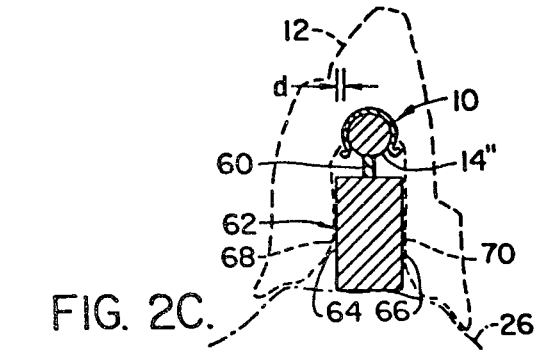

Referring to FIGS. 2A, 2B and 2C, there are shown three embodiments of retention bars. In the first preferred embodiment, the retention bar 14 is of circular transverse cross-section (FIG. 2A). In the second preferred embodiment of the invention, FIG. 2B, a retention bar 14' is characterized by an egg-shaped transverse cross-section, the smaller radius portion being on the opposing side of the clip 10.

FIG. 2C shows a retention bar 14" with an extension 62. The extension 62 is used for replacing lost bone and tissue and for filling in voids caused by birth defects and the like. The extension 62 attaches to the bar 14" by means of a relatively thin pedestal segment 60. The pedestal segment 60 is typically narrower than the bar 14" or the extension 62 and does not extend vertically more than about one-half millimeter. The extension 62 is thicker than the combined width of both the clip 10 and the bar 14" by an amount d on both sides thereof. The amount d is on the order of 0.2 mm. The inner walls 68 and 70 of denture 12 substantially ride against the enhanced width of the extension 62 on opposing faces 64 and 66 thereof thereby inhibiting lateral movement of the denture 12 about the bar 14". Movement of the denture 12 is substantially restricted to a vertical plane through the extension 62, pedestal segment 60 and bar 12.

The transverse cross-sectional shape of the retention bars 14, 14' determine the characteristics of circumferential and transverse play of the clip 10 relative to the bar 14, 14'. For example, the retention bar 14 of FIG. 2A permits greater circumferential and lateral play so that margins 20, 22 of denture 12 (all shown in phantom) are able to distribute a greater portion of a load of the denture 12 along the adjoining tissue 26 (shown in phantom) than for example a coupling system using an egg-shaped retention bar 14' (FIG. 2B). Under such circumstances the abutments 16, 18 are less subject to damage due to shock loading as caused by chewing and the like as compared to a coupling system where substantially all of the load is distributed to the abutmments 16, 18.

Figure 3:
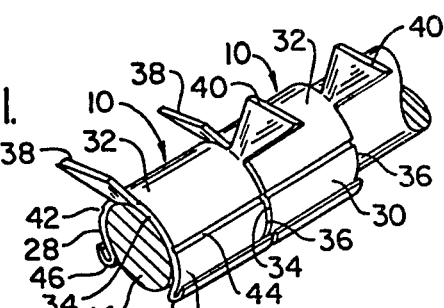
FIG. 3 is a perspective view of rider clips according to the invention mounted on a section of a bar.

Referring to FIGS. 2A, 2B and 3, clips 10 according to the invention are shown in greater detail. The clip 10 comprises an open tubular segment of a resilient material such as stainless steel or a gold alloy. The clip comprises three wall sections, a first side wall section 28, a second side wall section 30, and a dorsal wall section 32. The side wall sections 28, 30 are integral with the dorsal wall section and are inwardly arched such that the side wall sections 28, 30 oppose one another. The clip 10 is substantially symmetric about a longitudinal dorsal plane (not shown) bisecting the dorsal wall section 32.

On opposing ends 34, 36 and on opposite sides of the dorsal plane, there are first and second flaps 38, 40 protruding outwardly from the clip 10. In the preferred embodiment of the clip 10, the flaps 38, 40 are flared outwardly from the dorsal plane, thereby to provide a larger surface at the extreme ends for seating within the material of the denture 24 (FIG. 2A). It is to be understood that the outward flare of the flaps 38, 40 does not impinge across the dorsal plane so that clips 10 can abut one another end to end in a manner wherein the flaps 38, 40 overlap the dorsal wall section 32 of the abutting clip 10. In this manner, the clips 10 can be aligned in a compact longitudinal pattern and secured in relatively small and narrow areas of a denture 12 (FIG. 1) or the like.

Important features of the invention are first and second grooves 42, 44 along the boundary between the dorsal wall section 32 and the side wall sections 28, 30 respectively. The grooves 42, 44 are disposed on the outer surface of the clip 10 and define a point where lateral flexure of the side walls 28, 30 is concentrated, since the cross-section of the clip 10 is somewhat weakened by the relatively shallower wall thickness along the grooves 42, 44 as compared to the thickness of the clip 10.

The grooves 42, 44 serve another important function as explained hereinbelow with respect to FIGS. 4A and 4B, namely the grooves 42, 44 are block-out lines defining the level to which the clips 10 are permitted to be embedded in the denture 12 (FIG. 1). The side wall sections 28, 30 are therefore free to flex laterally a limited extent between the bar 14 and denture margins 20, 22, as is illustrated in FIGS. 2A or 2B.

Futher optional features of the invention are lap seams 46, 48 (FIGS. 2A, 3) along the longitudinal margins of the side wall sections 28, 30 respectively. The lap seams 46, 48, comprising a folded edge or like blunted margin, present a relatively blunt surface to confronting tissue and the like thereby minimizing the risks of damage to such underlying tissue. FIG. 2A is illustrative of a cross-section of the lap seams 46, 48 confronting underlying tissue 26.

Figure 4A:
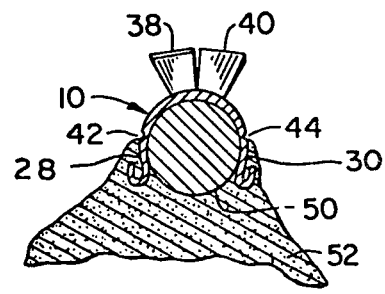
FIGS. 4A and 4B illustrate pertinent steps in a method for preparing a denture incorporating the retention clips of FIG. 3.
Figure 4B:
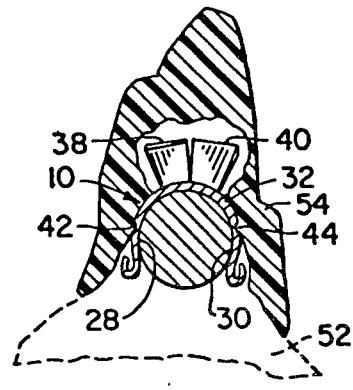

Turning now to FIGS. 4A and 4B, a method of making a denture is described which incorporates the clips according to the invention. The length of the retention area in the denture is first determined. This may be accomplished by constructing the retention bar or a model of the retention bar as a bar 50 as it is mounted in place to tooth abutments. The clips 10 are then mounted to the retention bar 50, as shown in FIG. 4A in cross-section. As many clips 10 are mounted to the bar 50 as is required for denture mounting, the clips 10 being mounted end to end with the end flaps 38, 40 overlapping, as required.

Thereafter, a filler material 52, such as plaster or rubber based material (e.g., "Rubber-Sep" manufactured by George Taub Company), is packed around the side wall sections 28, 30 of the clip 10 to the level of the grooves 42, 44, the designated block-out lines (FIG. 4A). The side wall sections 28, 30 are therefore totally immersed in the filler 52.

Referring now to FIG. 4B, the prosthetic teeth are then set with the denture mold material 54 invested over the clip 10 and filler material 52. The mold material 54, which is preferably an acrylic polymer, thereupon sets around the dorsal wall section 32 to the extrema of the block-out lines or grooves 42, 44. The flaps 38, 40 are embedded in the denture material 54, as shown in partial cutaway.

After setting, the filler 52 is expunged (FIG. 4B), thereby leaving the side wall portions 28, 30 exposed. The provision of the grooves 42, 44 as block-out lines and the use of an expungable filler 52 minimizes the risk that the denture maker, i.e., dentist or dental technician, will incorrectly set the clips 10 in the denture material. Moreover, the consequence in the use of the filler 52 assures that the side wall sections 28, 30 remain exposed and capable of subsequent adjustment, should adjustment be found to be necessary.

In the above process, the critical steps are the initial shrouding of the side wall sections of the clip 10 with a filler material, followed by the investing process in which the flaps 38, 40 are seated in the mold material 54, and the extraction of the filler material, thereby exposing the side wall sections to permit wall flexure.

Having thus explained the structure and method of the invention and having set forth the objects, applications, and advantages of the invention, it should be understood that improvements on this invention will be apparent to those of ordinary skill in the relevant art. Therefore, it is not intended that the invention be limited, except as indicated by the appended claims. For example, each of the embodiments may be utilized with a bar spacer disposed between the bar 14 and the clips 10. The spacer may be an elongate rod having a hemispherical transverse cross-section. The spacer may serve as a means for allowing vertical and rotational movement, thereby reducing stress on bone tissue and abutment.

What is claimed is:

1. A prosthetic device rider clip adapted to be secured to a bridge piece and operative to removably couple onto a retention bar having an arcuate transverse cross-section and secured to an abutment in a jaw, said clip comprising an open tubular segment of a resilient, substantially corrosion-resistant material, said segment being of a longitudinal extent not substantially exceeding the breadth of a tooth, and comprising a dorsal wall section, first and second inwardly arched side wall sections integral with said dorsal wall section and disposed opposing one another at a minimum separation of less than the diameter of the retention bar, and first and second retention flaps protruding outwardly from said opposing ends, wherein said dorsal wall section and said flaps are adapted to be secured within a casting of said bridge piece.

2. A prosthetic denture rider clip adapted to be secured to a bridge piece and operative to removably couple onto a retention bar having an arcuate transverse cross-section and secured to an abutment in a jaw, said clip comprising an open tubular segment of a resilient, substantially corrosion-resistant material, said segment being of a longitudinal extent not substantially exceeding the breadth of a tooth, and comprising a dorsal wall section, first and second inwardly arched side wall sections integral with said dorsal wall section and disposed opposing one another at a minimum separation of less than the diameter of the retention bar, and first and second grooves parallel with said dorsal plane and disposed on the outer surfaces of said tubular segment at boundaries of said side wall sections with said dorsal wall section, wherein said dorsal wall section is adapted to be secured within a casting of said bridge piece and said side wall sections are adapted to be free of said casting such that lateral flexure of said side walls is concentrated at said flexure grooves.

* * * * *